United States Patent
Fehse et al.

[11] Patent Number: 5,978,699
[45] Date of Patent: Nov. 2, 1999

[54] GUIDEWIRE THREADER

[75] Inventors: Jan Fehse, Berg; Eugen Hofmann, Zürich, both of Switzerland; Richard S. Kusleika, Eden Prairie; Richard L. Goodin, Blaine, both of Minn.

[73] Assignee: Schneider (Europe) GmbH, Bulach, Switzerland

[21] Appl. No.: 08/786,607

[22] Filed: Jan. 21, 1997

[30] Foreign Application Priority Data

Apr. 18, 1996 [EP] European Pat. Off. ............. 96106109

[51] Int. Cl.$^6$ .............................. A61B 5/00; A61M 25/00
[52] U.S. Cl. ........................................... 600/434; 600/585
[58] Field of Search ..................... 600/434, 585, 600/462, 463, 466, 467, 439, 210; 604/96, 280, 164; 606/210; 24/499, 487, 513, 514, 535, 545, 546, 547

[56] References Cited

U.S. PATENT DOCUMENTS

| | | | |
|---|---|---|---|
| 4,435,175 | 3/1984 | Friden | 604/264 |
| 4,838,880 | 6/1989 | Honma | 604/280 |
| 4,917,103 | 4/1990 | Gambale et al. | 604/164 |
| 4,922,923 | 5/1990 | Gambale et al. | 128/772 |
| 5,026,351 | 6/1991 | Dizon | 604/164 |
| 5,031,636 | 7/1991 | Gambale et al. | 128/772 |
| 5,137,288 | 8/1992 | Starkey et al. | |
| 5,191,888 | 3/1993 | Palmer et al. | 600/585 |
| 5,234,002 | 8/1993 | Chan | 128/772 |
| 5,318,541 | 6/1994 | Viera et al. | 604/164 |
| 5,320,613 | 6/1994 | Houge et al. | 604/283 |
| 5,361,777 | 11/1994 | Sellers | 600/585 |
| 5,439,012 | 8/1995 | D'Agostino | 606/210 |
| 5,449,362 | 9/1995 | Chaisson et al. | 606/108 |
| 5,456,699 | 10/1995 | Armstrong | 606/108 |
| 5,634,475 | 6/1997 | Wolvek | 600/585 |

FOREIGN PATENT DOCUMENTS

| | | |
|---|---|---|
| 0328760A3 | 8/1989 | European Pat. Off. . |
| 2180454A | 4/1987 | United Kingdom . |
| 96/02294 | 2/1996 | WIPO . |

*Primary Examiner*—Richard J. Apley
*Assistant Examiner*—Justine R. Yu
*Attorney, Agent, or Firm*—Crompton, Seager & Tufte, LLC

[57] ABSTRACT

A guidewire threader to facilitate insertion of the proximal end of a guidewire into the distal end of a catheter including two clamping pieces each of which has the shape of a lever having two arms and are hinged to each other for pivoting about a common axis between a closed clamp position and an open release position. A spring maintains clamping surfaces, each of which is provided on one arm of each clamping piece, positively in contact with each other in the clamp position. The clamping surfaces in their condition in contact with each other define a passage oriented roughly parallel to the common pivot axis open at both ends, the passage containing a section having an interior dimension corresponding to the outer diameter of the catheter and which is flared funnel-shaped at both of its ends. In the release position, the clamping surfaces open the passage in the lateral direction for removal of the guidewire.

4 Claims, 10 Drawing Sheets

GUIDEWIRE THREADER

BACKGROUND OF THE INVENTION

The invention relates to a guidewire threader that facilitates insertion of the proximal end of a guidewire into the distal end of a catheter.

When a patient is subjected to a vascular treatment necessitating employment of a catheter, a guide catheter is first inserted into the vessel in which the catheter is to be employed, after which a guidewire is introduced in the guide catheter. Via this guidewire, the actual treatment catheter is then advanced up to the point at which the treatment procedure is to be implemented. The treatment catheter has for this purpose a passage beginning at its tip which extends over a certain portion or over the full length of the catheter and serves to receive the guidewire. This means that the proximal end of the guidewire needs to be inserted in the opening of this passage at the distal end of the catheter. Since the passage in the treatment catheter has an inner diameter which is only slightly greater than the outer diameter of the guidewire, insertion is difficult, and it needs to be taken into account that the complete treatment procedure should be implemented in as short a time as possible to reduce the stress on the patient.

Devices relating to medical wire insertion are disclosed for instance in U.S. Pat. Nos. 4,838,880 and 5,320,613.

The invention is thus based on the object of defining a guidewire threader which is simple, cost-effective to manufacture, permits introduction of the guidewire speedily and safely into the distal end of the catheter, and which is subsequently easily removable from the guidewire.

All documents cited herein, including the foregoing, are incorporated herein by reference in their entireties for all purposes.

SUMMARY OF THE INVENTION

Accordingly, when using the guidewire threader according to the invention, the distal end of the catheter is inserted from one side into the passage formed between the clamping surfaces, and the proximal end of the guidewire is then introduced from the other side into the passage which is flared funnel-shaped at both ends. In this way, simple and speedy insertion of the guidewire into the catheter is made possible. After the guidewire has been introduced into the catheter, the passage can be opened so that the guidewire threader can be moved away laterally from the guidewire and catheter so that it no longer disturbs further treatment.

Also, when using another embodiment of the guidewire threader, the distal end of the catheter is introduced into one end of the guidewire threader, and the guidewire is inserted in the funnel-shaped flared end until it is located in the catheter. Since the slot extends over the full length of the guidebody, the guidewire threader can subsequently be removed laterally from the guidewire and catheter so that it no longer disturbs further treatment.

In sum, the present invention relates to a guidewire threader to facilitate insertion of the proximal end of a guidewire into the distal end of a catheter including two clamping pieces each of which has the shape of a lever having two arms and are hinged to each other for pivoting about a common axis between a closed clamp position and an open release position. A spring maintains the clamping surfaces, each of which is provided on one arm of each clamping piece, positively in contact with each other in the clamp position. The clamping surfaces in their condition in contact with each other define a passage oriented parallel to the common pivot axis and are open at both ends. The passage contains a section having an interior dimension corresponding to the outer diameter of the catheter and which is flared funnel-shaped at both of its ends. The clamping surfaces in the release position laterally opening the passage for removal of the guidewire. The passage may be formed by a depression being provided in one half of each clamping surface, the cross-section of the depression corresponding to the cross-section of the passage to be generated and the axial length of which corresponds to half the length of the passage, the plane of the clamping surface coinciding in its middle portion of the half not provided with a depression with the bottom of the adjoining depression in the other half. The passage may have a square cross-section. The spring may be a U-shaped bent leaf spring along the bend line of which a pin is provided which comprises two sections protruding from both sides of the leaf spring, wherein on the sides of the clamping pieces carrying the clamping surface, gripping elements are provided which are latchable with the pin such that the pin forms the common pivot axis of the clamping pieces and wherein the leaf spring is maintained tensioned between the two clamping pieces, the leaf spring in this position spreading apart two arms of the clamping pieces and thereby maintaining the clamping surfaces in contact with each other. The clamping pieces may be configured as identical injection molded parts. The guidewire threader or leaf spring may further include a portion adapted to hold at least a portion of a catheter or guidewire.

The invention also relates to a guidewire threader to facilitate insertion of the proximal end of a guidewire into the distal end of a catheter including a guidebody including one section for receiving the catheter centered and one funnel-shaped flared section. The guidebody being provided with a slot extending over its full axial length. The guidebody may be a tubular guidebody.

The invention also relates to a guidewire threader including a one-piece body having a front end, back end, top section and bottom section. The top section and bottom section each extend outwardly from the back end, are integrally hinged to each other at a common pivot axis, are at least partially in contact with each other at the front end, and define a passage extending therethrough. The top section and bottom section are adapted to separate and open the passage upon application of a predetermined pressure on the back end of the top section and bottom section. The passage may have a square cross-section. The passage may be formed by a depression being provided in one half of each top section and bottom section. The passage may be at least partially open at both ends. The passage may contain a portion having an interior dimension corresponding to the outer diameter of the catheter and which is flared funnel-shaped at both of its ends. The passage may have one or more funnel shaped portions. The passage may be substantially parallel to the common pivot axis. The common pivot axis may have resiliency and be adapted to maintain the passage in a closed position in a natural state or restore the passage to a closed position when pressure is removed. The body may be molded from one piece. The top section and bottom section may have internal mating surfaces facing one another that are nonplanar. At least a portion of the internal mating surfaces may be in the shape of a waveform or in the shape of a curve.

The invention also relates to a method of inserting a guidewire into a catheter including the steps of placing a guidewire threader over a prefolded balloon communicating with a distal end of a catheter and forming a balloon catheter and guidewire threader combination to provide shape retention and protection of the prefolded balloon during shipment, loading the balloon catheter and guidewire threader combination over the guidewire proximal end, and removing the guidewire threader from the balloon catheter and guidewire through at least a slot extending over the guidewire threader axial length. The slot may be a permanent slot or a variable sized slot formed from opening a passageway in the guidewire threader. The method of inserting a guidewire into a catheter may include the step of removing a sheath from a balloon catheter prior to placing the guidewire threader over the prefolded balloon.

The invention also relates to a method of inserting a guidewire into a catheter including the steps of placing a guidewire threader onto the distal end of a catheter and forming a catheter and guidewire threader combination to provide protection of the distal end of the catheter during shipment, loading the catheter and guidewire threader combination over a proximal end of the guidewire, and removing the guidewire threader from the catheter and guidewire. The guide wire threader may be removed from the catheter and guidewire by a permanent slot or a variable sized slot formed from opening a passageway in the guidewire threader.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

DETAILED DESCRIPTION OF THE INVENTION

Figure 1:
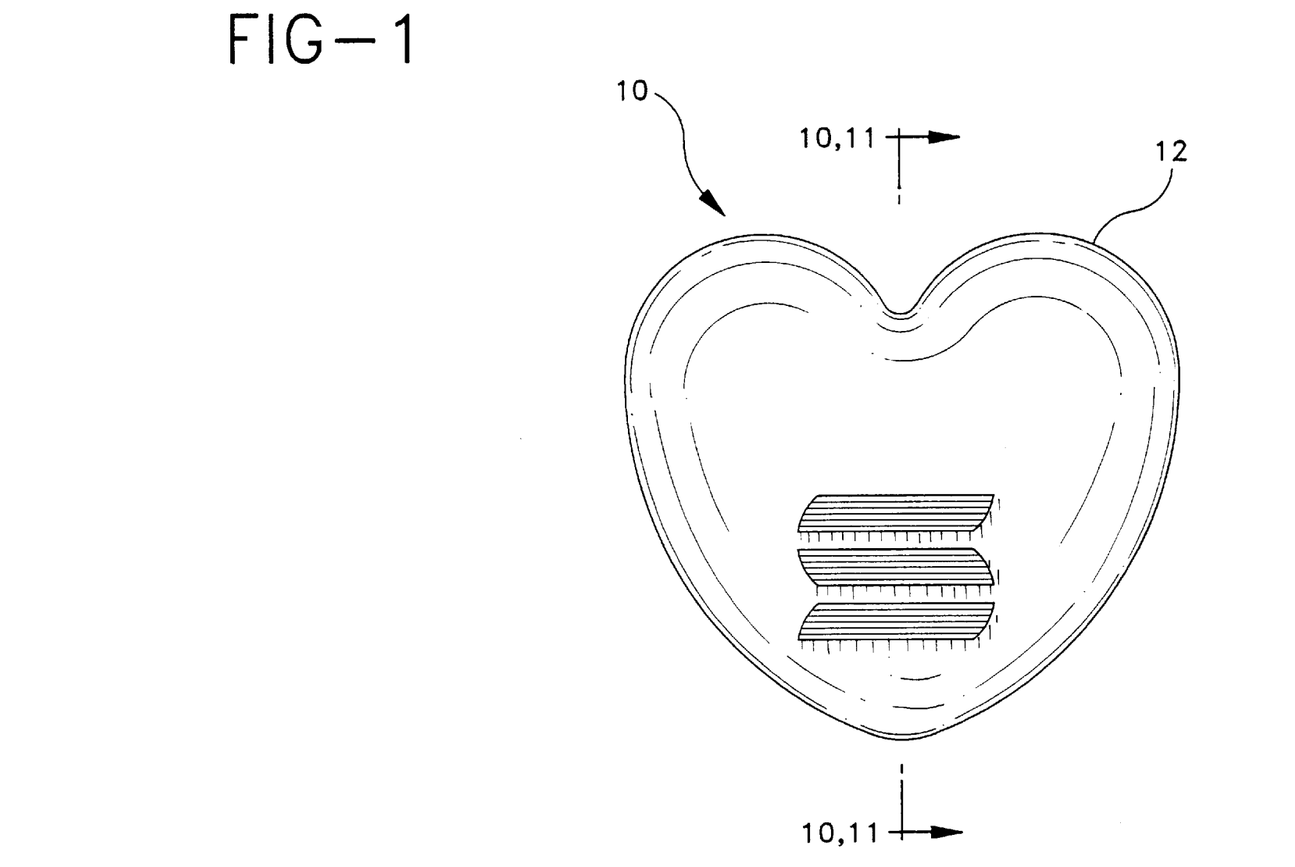
FIG. 1 is an overall view of the guidewire threader according to the invention.

The guidewire threader 10, illustrated in FIG. 1 consists of two identical clamping pieces 12a, 12b which have a heart-shaped contour. Two of these clamping pieces 12a, 12b may be joined together like a clothes clamp. How and by what means this joining together is done is explained with reference to FIGS. 2 and 3 which show the internal sides of the clamping pieces 12a, 12b facing away in FIG. 1.

Figure 2:
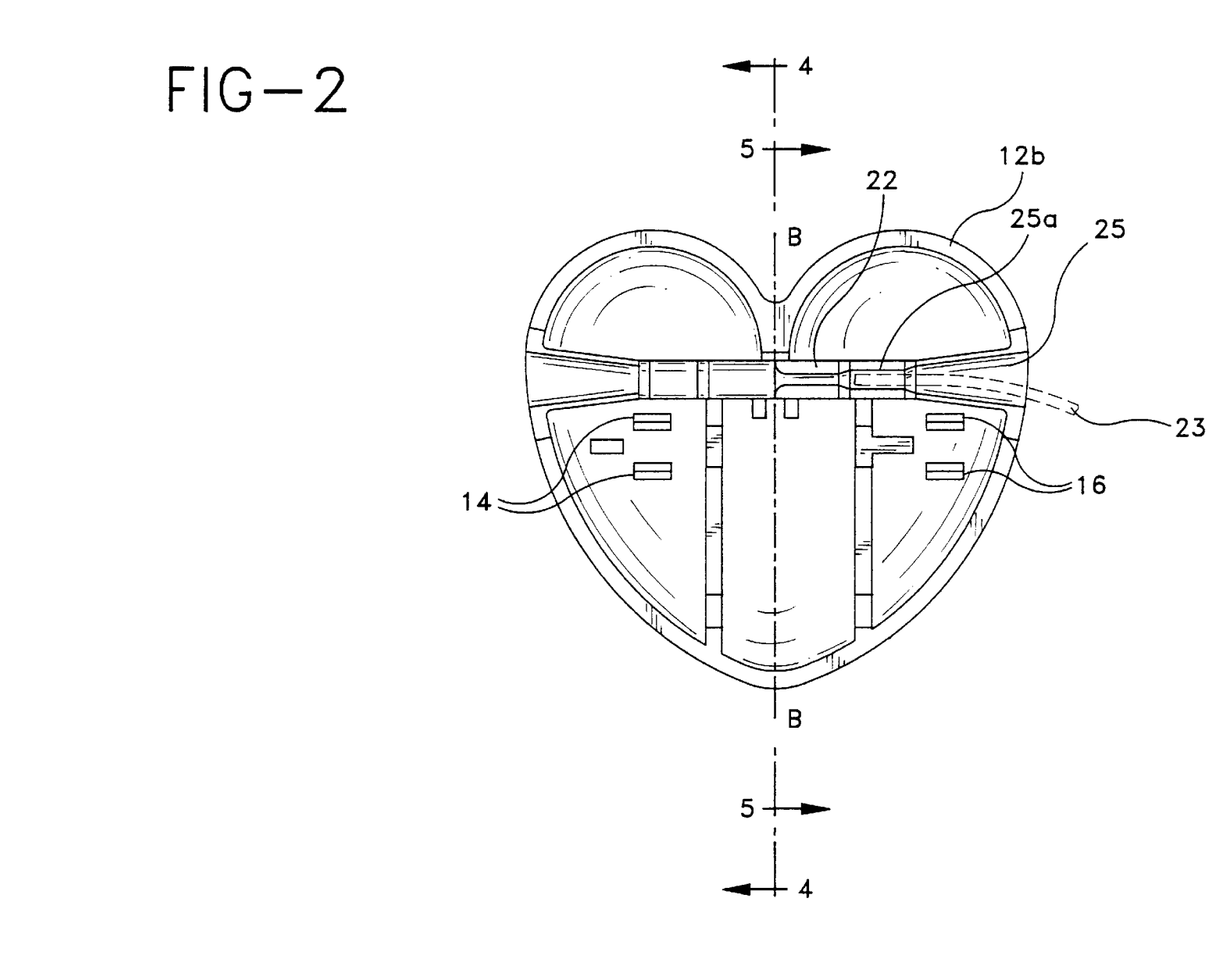
FIG. 2 is a view of the internal surface of one of the two clamping pieces of the guidewire threader of FIG. 1.
Figure 4:
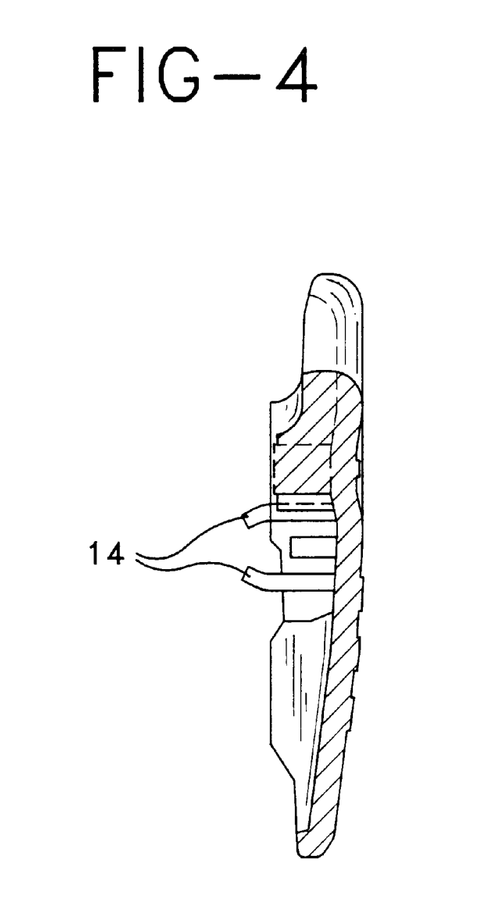
FIG. 4 is a section along the line 4—4 of FIG. 2.
Figure 5:
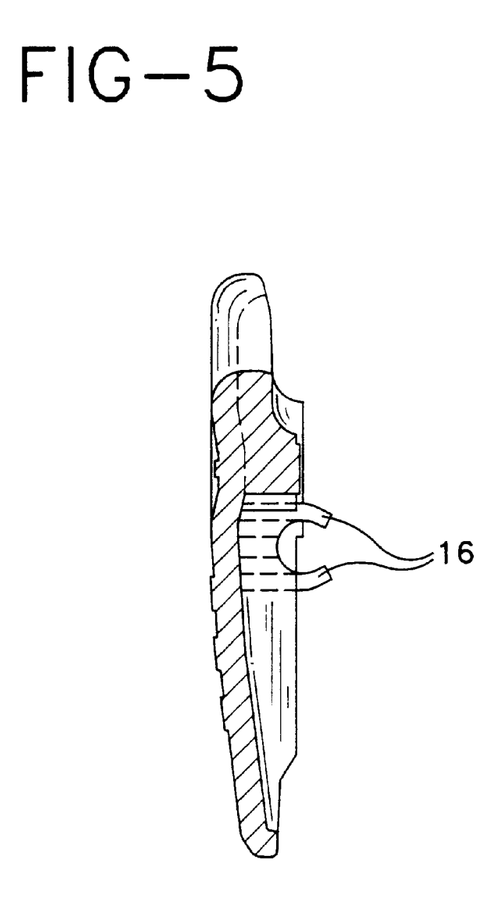
FIG. 5 is a section along the line 5—5 of FIG. 2.
Figure 6:
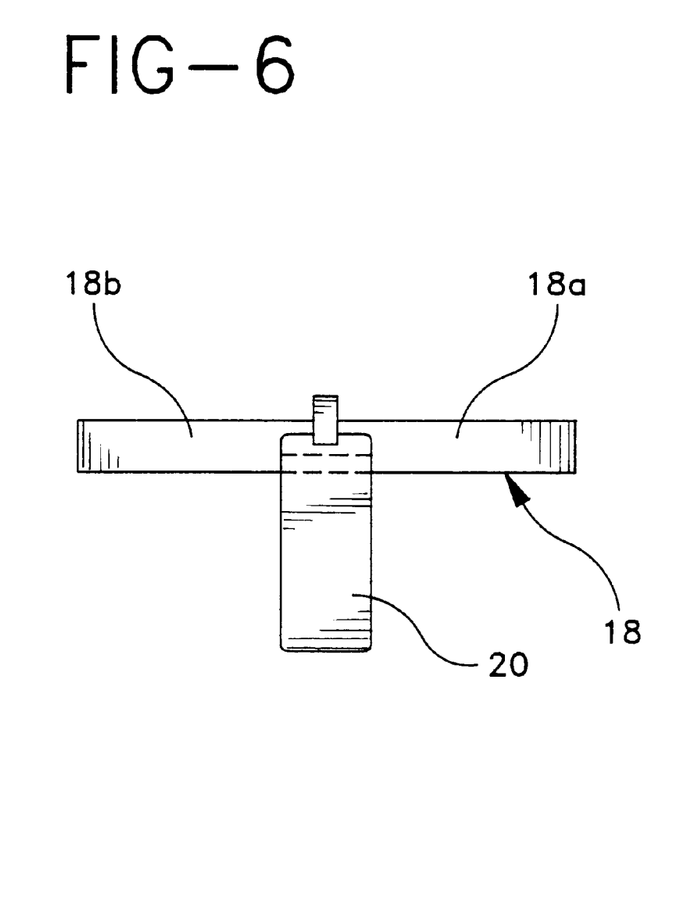
FIG. 6 is a view of a spring and pin used in the guidewire threader of FIG. 1.
Figure 7A:
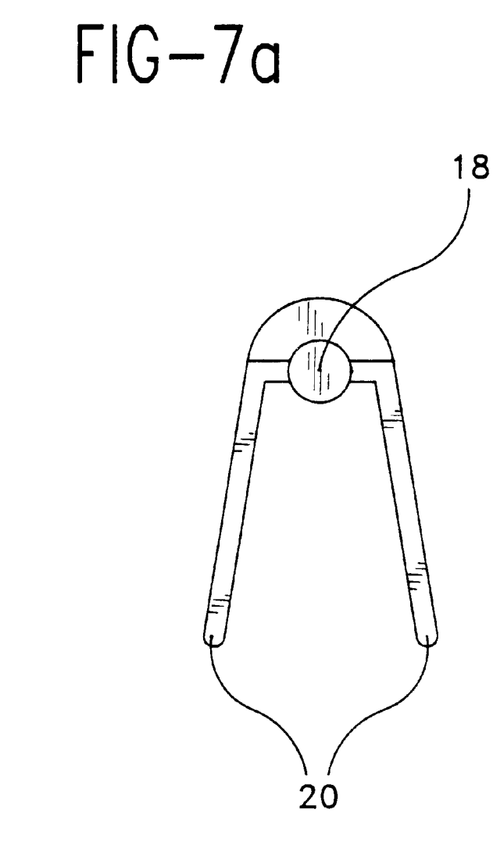
FIG. 7a is a side view of the spring and pin of FIG. 6.
Figure 7B:
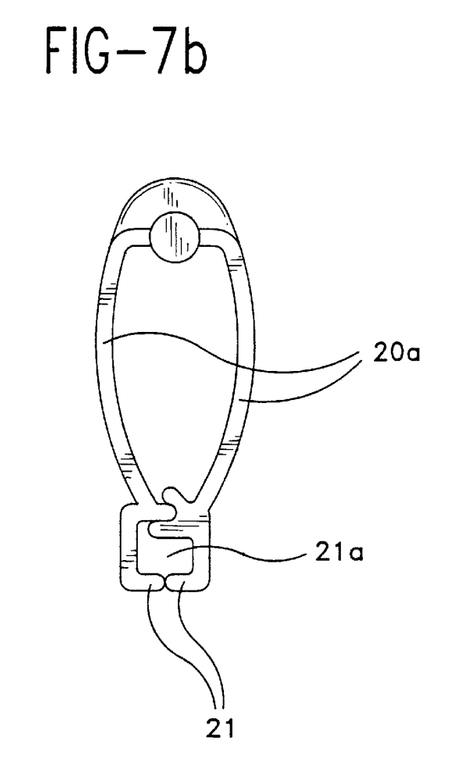
FIG. 7b is a side view of another embodiment of the spring and pin in a natural state.
Figure 7C:
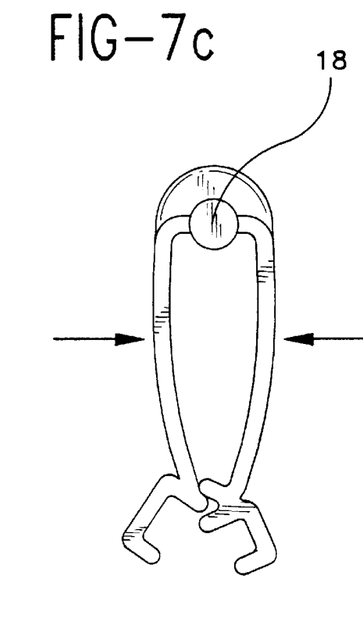
FIG. 7c is a side view of another embodiment of the spring and pin of FIG. 7b with pressure exerted on the spring.
Figure 7D:
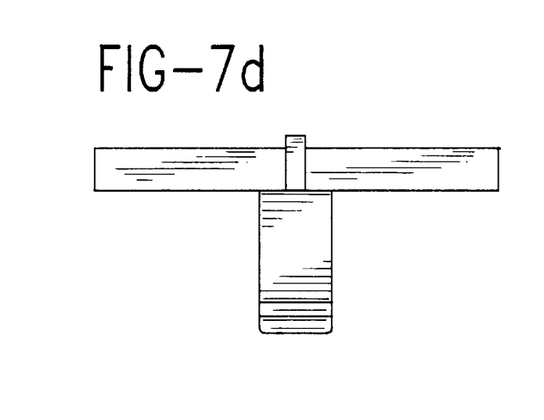
FIG. 7d is a front view of the spring and pin of FIG. 7b.

In FIG. 2, gripping elements 14, 16 are provided on the internal surface which as shown by the section views of FIGS. 4 and 5 each consist of two arcuate pieces between which a pin 18 may be pressed that carries in its middle portion a leaf spring 20. The combination of the pin 18 and the leaf spring 20 is illustrated in FIG. 6, the side view of FIG. 7a making it evident that the leaf spring 20 is configured U-shaped and is connected to the pin 18 in the region of its bend so that two sections 18a and 18b extend away from this bend. FIGS. 7b–7d illustrate another embodiment of the leaf spring 20 connected to the pin 18. However, in this embodiment, spring members 20a have a holding portion 21 on the end away from the pin 18 which allows a catheter or guidewire to be clipped in the holding portion 21 opening 21a. When pressure is applied to the spring members 20a as illustrated in FIG. 7c, the holding portion members 21 are forced together which creates an opening 21a and allows the catheter or guidewire to be place in the opening 21a or removed from the opening 21a. When pressure is removed from the spring members 20a or the spring members 20a is in a natural state as illustrated in FIG. 7b, the holding portion 21 is in a closed position and may contain the catheter or guidewire in the opening 21a. FIG. 7d shows a front view of the spring member 20a in a natural state. The holding portion 21 helps to keep the catheter or guidewire organized.

Figure 3:
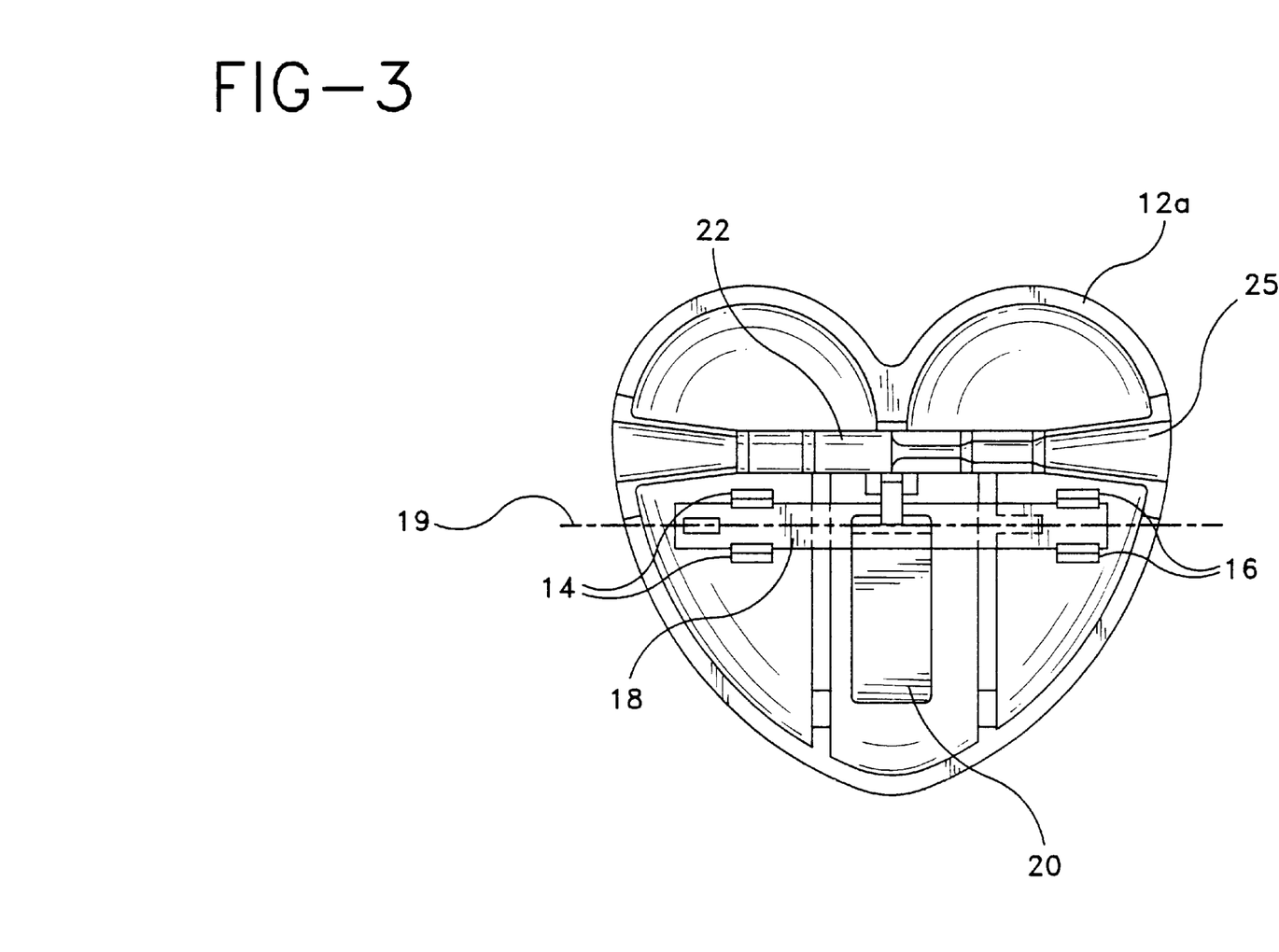
FIG. 3 is another such view as in FIG. 2 with a clamp spring inserted.

From FIG. 2, it is evident that the gripping elements 14 and 16 are located differently spaced from the center axis B—B of the clamping piece 12. In clamping piece 12a, as shown in FIG. 3, the pin 18 is inserted with the leaf spring 20 in the gripping elements 14 and 16. Then, a second clamping piece 12b, as illustrated in FIG. 2, with gripping elements 14 and 16, can also be pressed onto the pin 18. The gripping element 14 of the clamping piece 12b, illustrated in FIG. 2, then being located to the left alongside the gripping elements 16 of the clamping piece 12a of FIG. 3 on the pin 18, while the gripping elements 16 of the clamping piece 12b of FIG. 2 are located on the pin 18 to the left alongside the gripping elements 14 of the clamping piece 12a illustrated in FIG. 3. In this way, both clamping pieces 12a, 12b are fixedly latched to the pin 18 and the leaf spring 20, due to its U-shape thus acts against the clamping pieces 12a, 12b so that their ends located at the bottom in FIGS. 2 and 3 are spread apart. In this arrangement, the clamping pieces 12a, 12b behave like two-armed levers, the pivot axis of which is formed by the axis 19 of the pin 18. They are movable between a closed clamp position and an open release position.

Figure 8:
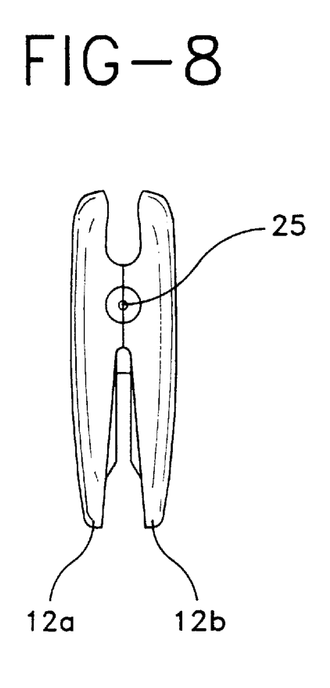
FIG. 8 is a side view of a guidewire threader with the passage closed.
Figure 9:
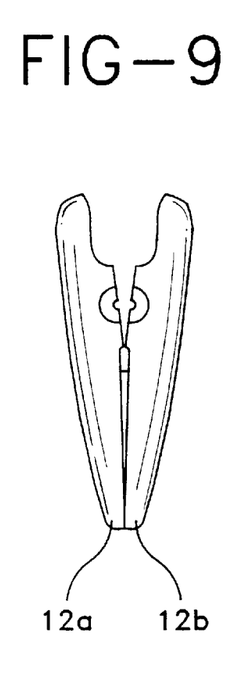
FIG. 9 is a side view of a guidewire threader with the passage open.
Figure 10:
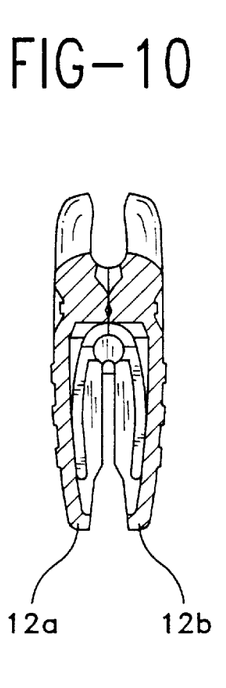
FIG. 10 is a section of the guidewire threader taken along the line 10—10 of FIG. 1 with the passage closed.
Figure 11:
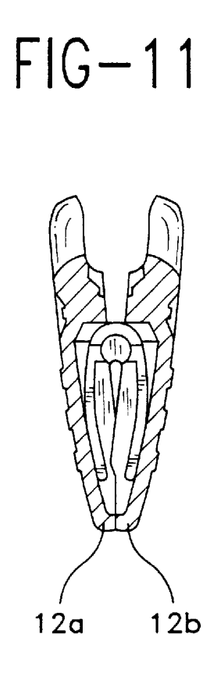
FIG. 11 is a section of the guidewire threader taken along the line 11—11 of FIG. 1 with the passage open.

In the side view of FIG. 8, two clamping pieces 12a, 12b are connected to each other by latching on the pin 18 and are illustrated in the clamp position in which the ends located at the bottom in FIG. 8 of the leaf spring 20 are spread apart, whereby to assist distinguishing the clamping pieces are denoted 12a and 12b. When pressure is exerted on the sections of the clamping pieces 12a, 12b located at the bottom against the force of the leaf spring 20, the two clamping pieces 12a, 12b pivot into the release position illustrated in FIG. 9. FIGS. 10 and 11 show the guidewire threader 10 in the positions of FIGS. 8 and 9, but each in sections along the line 10—10 and 11—11 of FIG. 1.

Figure 12:
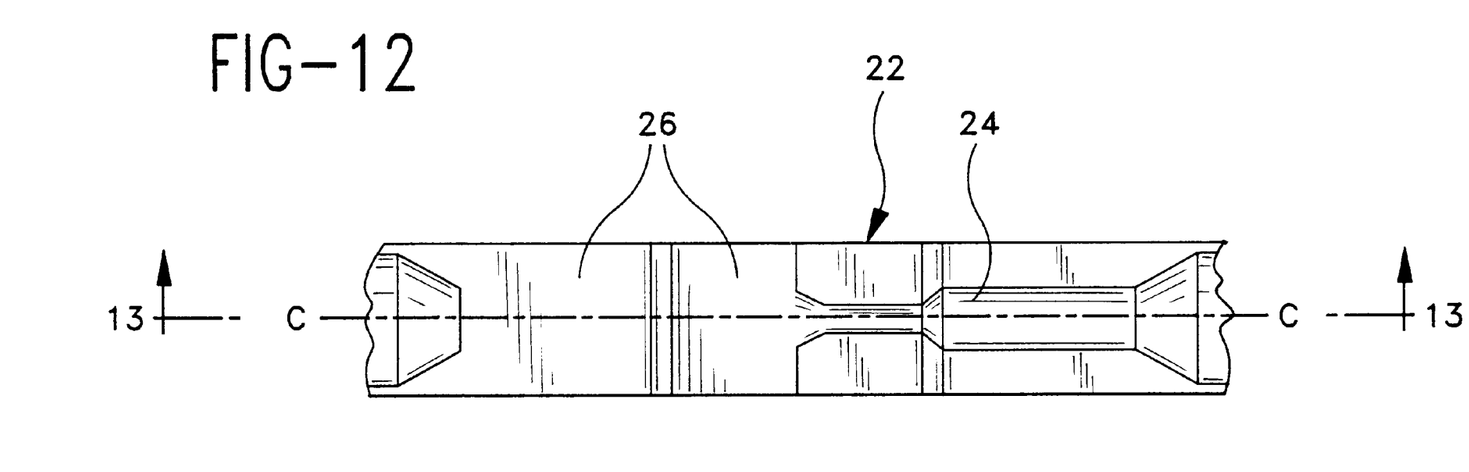
FIG. 12 is a partial elevation view of the clamping surface of the clamping piece of FIG. 2 and FIG. 3 in which the depression provided in this clamping surface is evident.
Figure 13:
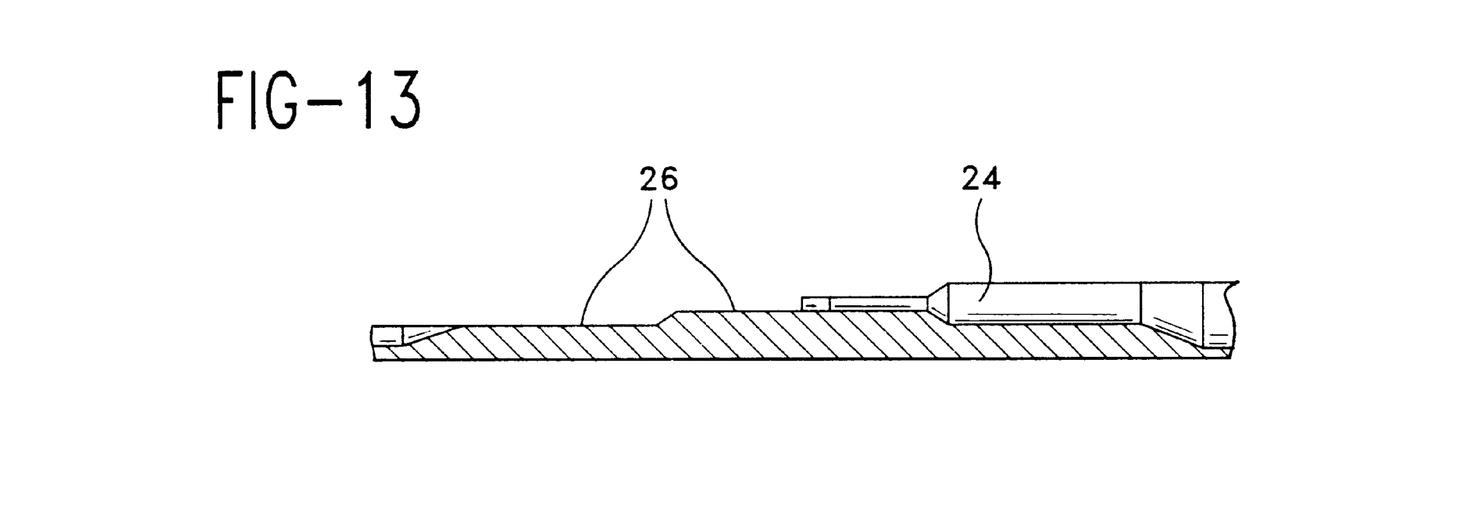
FIG. 13 is a section along the line 13—13 of FIG. 12 to illustrate the position of the depression in the clamping surface.

In FIG. 2, in a middle portion of the clamping piece 12b, a clamping surface 22 is evident which is maintained in the clamping position of the guidewire threader 10 of FIG. 8 by the leaf spring 20 in contact with the corresponding clamping surface 22 of the other clamping piece 12a. In the clamping surface 22, in the half located on the right in FIG. 2, a depression is provided which is flared funnel-shaped towards the end located on the right in FIG. 2 of the clamping surface 22. A magnified section of the clamping surface 22 with the depression 24 provided therein is illustrated in FIG. 12. FIG. 13 shows a section along the line 13—13 of FIG. 12, with only the section of the clamping piece 12 being illustrated in which the clamping surface 22 is located.

As is evident from FIG. 12, the depression 24 is flared in two steps, funnel-like towards the end located on the right in FIG. 12. Due to this step-like flaring, evident in FIG. 13, perpendicular to the longitudinal direction of the depression, a flaring also results in this perpendicular direction. In the half shown on the left in FIG. 12, the clamping surface 22 has a non-recessed planar surface. In the middle portion, this planar surface translates directly into the bottom of the first depression adjoining the middle on the right. This middle portion is followed by a further non-recessed portion of the clamping surface with a step transition.

In section 25a, the passage 25 has an interior dimension corresponding to the outer diameter of the catheter into which the guidewire is to be introduced.

When two identical clamping pieces 12a, 12b are placed one against the other by their internal surfaces, the part shown on the right in FIG. 12 of the clamping surface locates on the side shown on the left in FIG. 12 of the clamping surface. This means that the depression 24 of the one clamping piece 12 then constitutes an elongation of the depression 24 of the other clamping piece 12, thus resulting in a continuous passage in the direction of the center line C—C illustrated in FIG. 12. In this arrangement, the planar surface 26 shown on the left in FIG. 12 of the clamping surface 22 forms practically the cover for the depression 24 in the other clamping surface. Accordingly, when the two clamping pieces 12a, 12b are joined together, a continuous passage open at both ends, made up of two depressions 24 located in line materializes when the two clamping pieces 12a and 12b are urged by the leaf spring 20, as shown in FIG. 8, that their clamping surfaces are juxtaposed. When the guidewire threader 10 is brought into the release position, shown in FIG. 9, by pressure being exerted on the sections located at the bottom in this FIG. of the clamping piece, the passage is opened towards the top in the arrangement of FIG. 9.

The guidewire threader 10 as described is put to use in practical application as follows:

When treatment requires the use of a catheter and the guidewire is already inserted in the vessel to be treated, the proximal end of the guidewire then needs to be inserted into the distal end of the treatment catheter. To facilitate insertion, the distal end of the treatment catheter is introduced laterally as far as possible into the funnel-shaped flared end of the passage of the guidewire threader 10. The proximal end of the guidewire is introduced into the other funnel-shaped flared end of the passage of the guidewire threader 10 until it penetrates the distal end of the treatment catheter. Due to the centered position of the distal end of the treatment catheter, the guidewire can be introduced into the catheter with no appreciable difficulty so that no waste of time occurs in this phase of the treatment procedure. A treatment catheter 23, indicated by a dashed line in FIG. 2, is inserted into the passage 25 from the right. Its distal end is located in the portion 25a in which the interior dimension of the passage roughly corresponds to the outer diameter of the catheter.

Once the guidewire has been introduced into the treatment catheter 23, the guidewire threader 10 is no longer required. By pressing the ends located at the bottom in FIG. 8 of the clamping pieces 12a, 12b, the former are pivoted about the pin 18 against the action of the leaf spring 20 into the position illustrated in FIG. 9 so that the passage originally closed in the clamping surface 22 is opened. The guidewire threader 10 can then be removed directly laterally from the treatment catheter and from the inserted guidewire.

The clamping pieces 12a, 12b may be manufactured cost-effectively as injection molded items since they are identical, thus requiring only a single injection mold. Due to the special position of the gripping elements 14, 16 and the configuration of the clamping surface 22 along with the depression 24 formed therein, the clamping pieces 12a, 12b are to be manufactured totally identical.

Figures 14, 15:
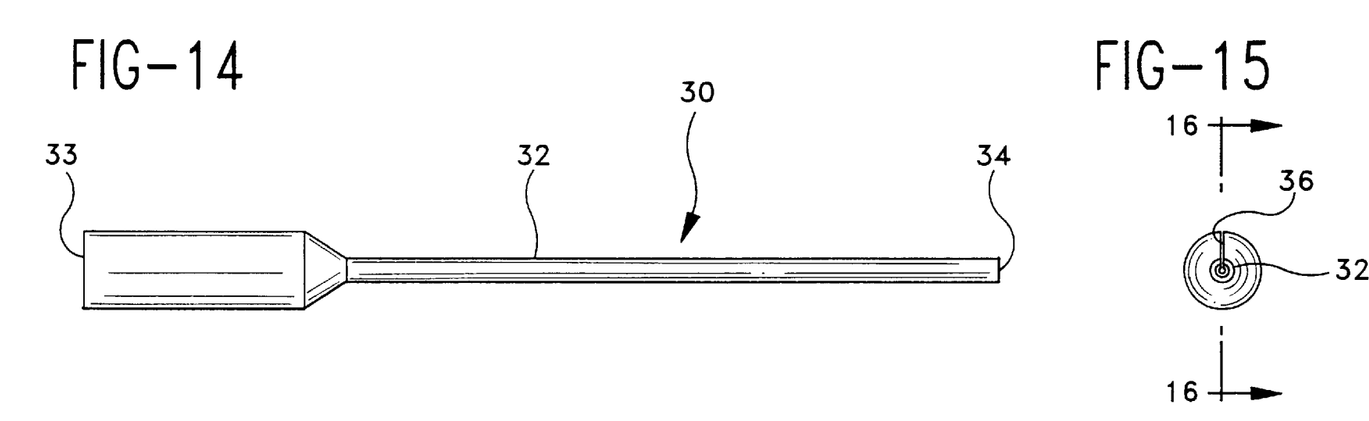
FIG. 14 is a side view of a guidewire threader according to a second embodiment of the invention.
FIG. 15 is a front view of the guidewire threader of FIG. 14 as seen from the right-hand side.
Figure 16:
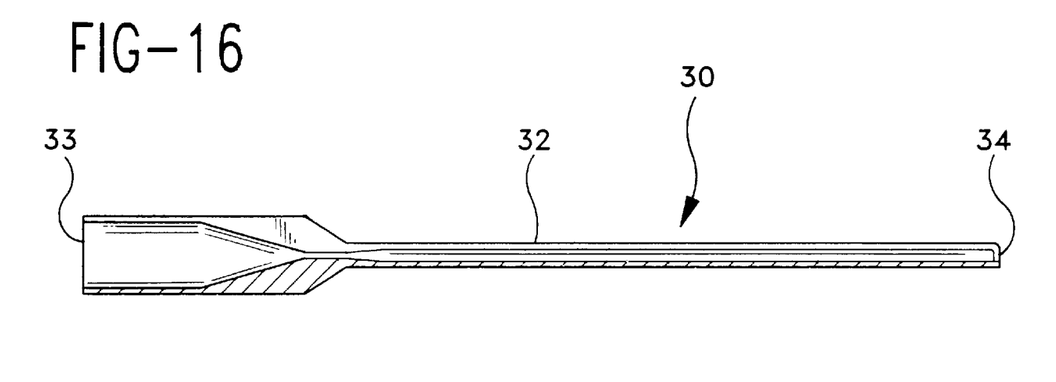
FIG. 16 is a section along the line 16—16 of FIG. 15.

A further embodiment of the invention is illustrated in the FIGS. 14, 15 and 16 and is denoted by the reference numeral 30. This guidewire threader 30 consists of a tubular guidebody 32 serving to receive the guidewire centered, which is flared funnel-shaped at one end 33. As shown by the front view in FIG. 15 and the section view along the line 16—16 in FIG. 15, a continuous slot 36 is provided in the wall of the guidebody 32.

When using the guidewire threader 30, the non-flared funnel-shaped end 34 of the guidebody 32 is pushed onto the distal end of the treatment catheter, the proximal end of the guidewire then being advanced into the funnel-shaped flared end 33 of the guidebody 32 until it is located in the treatment catheter. Due to the centered position of the distal end of the treatment catheter, insertion of the guidewire can be speedily implemented with no waste of time. On completion of insertion, the guidewire threader 30 can be removed distally from the catheter, off the balloon, then laterally from the guidewire, since the slot 36 allows the guidewire to emerge laterally from the guidebody 32.

The guidewire threader 30 is preferably shipped on the balloon catheter. The guidebody 32 serves as a sheath to preserve low balloon profile and to protect the balloon. When the guidewire threader 30 is already on the balloon, few separate steps are needed to use the guidewire threader 30.

Figure 17:
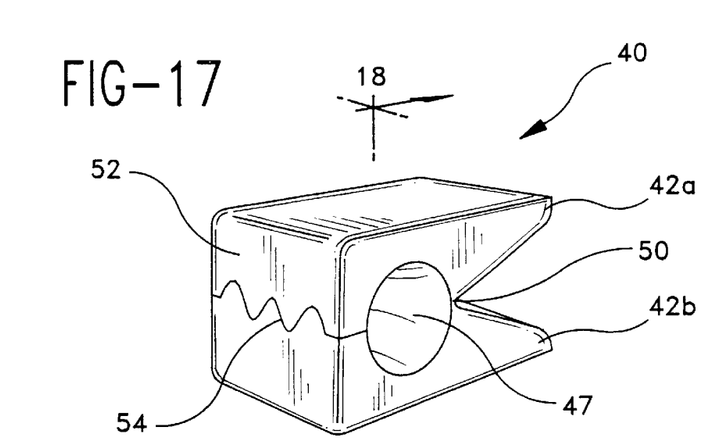
FIG. 17 is a view of a guidewire threader according to a third embodiment of the invention.
Figure 18:
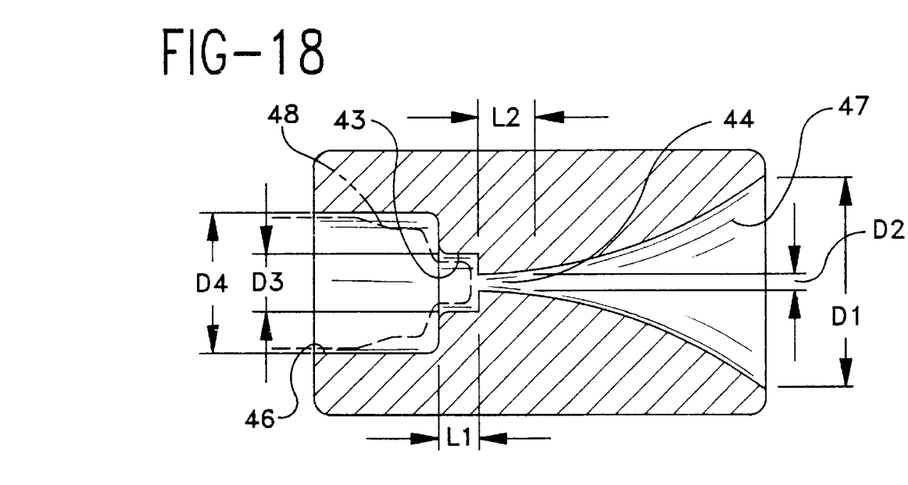
FIG. 18 is a section along the line 18—18 of FIG. 17.

Reference is made to FIG. 17 and 18 showing another embodiment of the invention made preferably from one molded piece of a rubber-like material having resiliency and is denoted by the reference numeral 40. The guidewire threader 40 preferably has a front end 52 with one or more wave-like edges 54 to help prevent the guidewire from slipping out of the threading passage 44 if the threader 40 is not fully closed.

The sheath of the balloon 48 fits in one end 46 of the threader 40 and the balloon tip fits in a notch 43 having a length L1 at least the length of the balloon tip and having a diameter D3 greater than and corresponding to the diameter of the balloon tip or catheter. The notch 43 is of sufficient size and shape, and may have square or tapered edges, to center the balloon 48 at the threading passage 44. The notch increases in size outwardly to end 46, and is of sufficient size and shape, and may have square or tapered edges to provide sufficient support to the balloon 48. The end 46 has a diameter D4 that is 1.25–3 times the diameter of the deflated balloon.

From the opposite end 47, the guidewire enters the threader 40 and is centered through the threading passage 44 into the tip of the balloon catheter. The dimensions of the threader 40 may vary depending on the catheter and guidewire diameters used. The guidewire entrance D1 is at least 5–10 times larger than the guidewire diameter, and may have square or tapered edges for centering of a guidewire. The length of the centering portion L2 of the threading passage 44 is preferably at least 3 times the balloon tip diameter.

The guidewire and catheter assembly can be removed laterally from the threader 40 when a predetermined pressure applied to pieces 42a, 42b causes the pieces 42a, 42b to pivot about the hinge 50 and causes the top section and bottom section of the front end 52 to open, exposing the threading passage 44. Thereafter, the guidewire threader 40 can be removed laterally from a catheter, balloon catheter and guidewire, since the slot size or lateral opening is relatively variable depending on the amount of pressure applied to pieces 42a, 42b.

The guidewire threader 10, 30, 40 may be manufactured cost-effectively from a plastic, rubber, metal, and materials known in the art and accompany every treatment catheter.

It will be evident from considerations of the foregoing that the guidewire threader 10, 30, 40 may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

We claim:

1. A guidewire threader to facilitate insertion of a proximal end of a guidewire into the distal end of a catheter comprising:

(a) two clamping pieces each of which has the shape of a lever having two arms and are hinged to each other for pivoting about a common axis between a closed clamp position and an open release position, the two clamping pieces each including a clamping surface;

(b) a spring which maintains the clamping surfaces positively in contact with each other in the clamp position;

(c) the clamping surfaces in their condition in contact with each other defining a passage oriented parallel to the common pivot axis, the passage having two ends and the passage being open at both ends;

(d) the passage containing a section having an interior dimension approximately corresponding to an outer diameter of the catheter, an elongate portion having an interior dimension approximately corresponding to an outer diameter of a guidewire, and the passage is flared funnel-shaped at both ends; and (e) the clamping surfaces in the release position laterally opening the passage for removal of the guidewire.

2. The guidewire threader of claim 1 wherein the spring is a U-shaped bent leaf spring along a bend line of which a pin is provided, the pin includes two sections protruding from both sides of the left spring, wherein on the sides of the clamping pieces carrying the clamping surface, gripping elements are provided which are latchable with the pin such that the pin forms the common pivot axis of the clamping pieces and wherein the leaf spring is maintained tensioned between the two clamping pieces, the leaf spring in this position spreading apart two arms of the clamping pieces and thereby maintaining the clamping surfaces in contact with each other.

3. The guidewire threader of claim 1 wherein the clamping pieces are configured as identical injection molded parts.

4. The guidewire threader of claim 1 wherein the spring further comprises a portion adapted to hold at least a portion of a catheter or guidewire.

* * * * *